United States Patent [19]

Walker

[11] 4,091,045
[45] May 23, 1978

[54] PROCESS FOR THE PURIFICATION OF LIQUID SORBENTS THAT COMPRISE BIMETALLIC SALT COMPLEXES

[75] Inventor: David G. Walker, Baytown, Tex.

[73] Assignee: Tenneco Chemicals, Inc., Saddle Brook, N.J.

[21] Appl. No.: 802,327

[22] Filed: Jun. 1, 1977

[51] Int. Cl.$^2$ ............................................. C07C 11/02
[52] U.S. Cl. ........................... 260/677 A; 260/671 R; 260/672 R; 260/672 T; 423/245
[58] Field of Search ................................... 260/677 A

[56] References Cited

U.S. PATENT DOCUMENTS

| | | | |
|---|---|---|---|
| 3,923,958 | 12/1975 | Turnbo et al. | 260/677 A |
| 3,927,176 | 12/1975 | Turnbo et al. | 260/677 A |
| 3,960,910 | 6/1976 | Sudduth et al. | 260/677 A |
| 4,014,950 | 3/1977 | Keyworth et al. | 260/677 A |

*Primary Examiner*—C. Davis
*Attorney, Agent, or Firm*—Evelyn Berlow

[57] ABSTRACT

Liquid sorbents that are solutions in an aromatic hydrocarbon or a halogenated aromatic hydrocarbon of a bimetallic salt complex having the generic formula $M_I M_{II} X_n$·Aromatic, wherein $M_I$ is a Group I-B metal, $M_{II}$ is a Group III-A metal, X is halogen, n is the sum of the valences of $M_I$ and $M_{II}$, and Aromatic is a monocyclic aromatic hydrocarbon or halogenated aromatic hydrocarbon having 6 to 12 carbon atoms and that contain alkylated aromatic compounds as impurities are purified by a process in which a portion of the liquid sorbent is subjected to two successive flash distillations, the first of which is carried out under atmospheric pressure to separate a distillate that is rich in the aromatic hydrocarbon or halogenated aromatic hydrocarbon and the second of which is carried out under subatmospheric pressure to separate a distillate that is rich in alkylated aromatic compounds, the residue of the distillation is reconstituted by adding aromatic hydrocarbon or halogenated aromatic hydrocarbon to it, and the reconstituted portion of the sorbent is combined with the remainder of the sorbent.

10 Claims, No Drawings

PROCESS FOR THE PURIFICATION OF LIQUID SORBENTS THAT COMPRISE BIMETALLIC SALT COMPLEXES

This invention relates to a process for the purification of liquid sorbents that are used to separate olefins from gas streams. More particularly, it relates to a process for the separation of alkylated aromatic compounds from liquid sorbents that contain certain bimetallic salt complexes.

Bimetallic salt complexes that have the generic formula $M_I M_{II} X_n \cdot$Aromatic, wherein $M_I$ is a Group I-B metal, $M_{II}$ is a Group III-A metal, X is halogen, $n$ is the sum of the valences of $M_I$ and $M_{II}$, and Aromatic is a monocyclic aromatic hydrocarbon or halogenated aromatic hydrocarbon having 6 to 12 carbon atoms, are known to be useful in the separation from gas mixtures of such complexible ligands as olefins, acetylenes, aromatics, and carbon monoxide. For example, in U.S. Pat. No. 3,651,159, Long et al. disclosed a process in which a sorbent solution of a cuprous aluminum tetrahalide in toluene was used to separate ethylene, propylene, and other complexible ligands from a gas feedstream. The complexed ligands were recovered by ligand exchange with toluene. The resulting solution of cuprous aluminum tetrahalide in toluene was recycled and used to separate additional quantities of the complexible ligands from the gas feedstream.

In processes such as that disclosed by Long et al. in which a ligand sorbent containing a bimetallic salt complex is recycled without purification and is used for long periods of time, there is a gradual increase in the amounts of reaction by-products and other impurities in it until sufficient impurities are present to interfere with the efficient operation of the process. For example, when the ligand sorbent is contacted with a gas stream that contains an olefin having 2 to 4 carbon atoms, some of the olefin reacts with the aromatic hydrocarbon or halogenated aromatic hydrocarbon in the sorbent to form alkylated aromatic compounds and some undergoes polymerization to form olefin oligomers. Attempts to inhibit the polymerization and alkylation reactions, for example, by the addition of ammonia or another basic compound to the sorbent, have been unsuccessful because they failed to reduce the amounts of by-products formed or because they interfered with the efficient operation of the process.

In U.S. Pat. No. 4,014,950, Keyworth et al. disclosed a process in which the polyalkylated aromatic compounds and olefin oligomers that are present as impurities are removed from a liquid sorbent by contacting the sorbent with an organic solvent in which the impurities are soluble and with which the liquid sorbent is immiscible and separating a solution of the impurities in the sorbent-immiscible organic solvent from the liquid sorbent.

This invention relates to an improved process for the purification of liquid sorbents. In this process, which is more efficient and more economical to operate than that disclosed in U.S. Pat. No. 4,014,950, a portion of the liquid sorbent that contains the alkylated aromatic compounds that are formed as reaction by-products when a gas feedstream that contains at least one olefin having 2 to 4 carbon atoms is contacted with a liquid sorbent that is a solution of the bimetallic salt complex $M_I M_{II} X_n \cdot$Aromatic in an aromatic hydrocarbon or an aromatic halogenated hydrocarbon, is removed from the system in which the liquid sorbent is being used to remove olefins from a gas feedstream, purified by a two-stage distillation that removes from it substantial amounts of aromatic hydrocarbons or halogenated aromatic compounds and alkylated aromatic compounds, reconstituted by the addition to it an aromatic hydrocarbon or a halogenated aromatic hydrocarbon, and returned to the system. Liquid sorbent which has been purified in this way can be used for long periods of time without danger of build-up of amounts of reaction by-products that interfere with the operation of the olefin separation procedure and make necessary the replacement of the liquid sorbent and the cleaning of the apparatus.

The liquid sorbents that are purified by the process of this invention are solutions of a bimetallic salt complex in an aromatic hydrocarbon or a halogenated aromatic hydrocarbon that contain alkylated aromatic hydrocarbons, alkylated halogenated aromatic hydrocarbons, and/or olefin oligomers. The bimetallic salt complexes in the liquid sorbents have the generic formula $M_I M_{II} X_n \cdot$Aromatic. $M_I$ is a Group I-B metal; that is, copper, silver, or gold. Copper (I) is the preferred metal. $M_{II}$ is Group III-A metal; that is boron, aluminum, gallium, indium, or thallium. Boron and aluminum are the preferred metals, aluminum being particularly preferred. X is halogen, i.e., fluorine, chlorine, bromine, or iodine; it is preferably chlorine or bromine. The sum of the valences of $M_I$ and $M_{II}$ is represented by $n$. Aromatic is a monocyclic aromatic hydrocarbon or halogenated aromatic hydrocarbon having 6 to 12 carbon atoms, and preferably 6 to 9 carbon atoms, such as benzene, toluene, ethylbenzene, xylene, mesitylene, chlorobenzene, bromobenzene, iodobenzene, dichlorobenzene, dibromobenzene, chlorotoluene, bromotoluene, iodotoluene, or chloroxylene. It is preferably benzene or toluene. Illustrative of these bimetallic salt complexes are the following: $CuBF_4 \cdot$benzene, $CuBCl_4 \cdot$benzene, $AgBF_4 \cdot$mesitylene, $AgBCl_4 \cdot$xylene, $AgAlCl_4 \cdot$xylene, $AgAlBr_4 \cdot$bromobenzene, $CuGaCl_4 \cdot$toluene, $CuInI_4 \cdot$1,2-dichlorobenzene, $CuTlI_4 \cdot$p-chlorotoluene, and the like. The preferred bimetallic salt complexes are $CuAlCl_4 \cdot$benzene, $CuAlCl_4 \cdot$toluene, and $CuAlBr_4 \cdot$benzene. The aromatic hydrocarbon or halogenated aromatic hydrocarbon in which the bimetallic salt complex is dissolved is usually and preferably the same as that used in the preparation of the bimetallic salt complex, but if desired it may be a different one. The total amount of aromatic hydrocarbon or halogenated aromatic hydrocarbon in the liquid sorbent, that is, the amount in the bimetallic salt complex plus the amount used as solvent, is at least 10 mole percent of the amount of the bimetallic salt $M_I M_{II} X_n$ that is present. It is preferred that the amount of aromatic hydrocarbon or halogenated aromatic hydrocarbon be 100 to 450 mole percent of the amount of the bimetallic salt. The particularly preferred liquid sorbents contain 25 to 75 percent by weight of $CuAlCl_4 \cdot$benzene in benzene.

When a gas feedstream that contains at least one olefin having 2 to 4 carbon atoms and optionally one or more other complexible ligands is brought into contact with one of the aforementioned liquid sorbents, the olefin and any other complexible ligands in the feedstream react with the liquid sorbent to form a reaction mixture that comprises complexes of these ligands with the bimetallic salt complex. The reaction mixture is then heated or treated with another complexible ligand to displace the olefin and other complexible ligands from it. The stripped liquid sorbent is recycled to the system where it is used to remove additional amounts of olefins and other complexible ligands from the gas feedstream.

In addition to reacting with the liquid sorbent to form complexes, the olefins in the gas feedstream react with the aromatic hydrocarbon or halogenated aromatic hydrocarbon in the liquid sorbent to form alkylated aromatic compounds that have the structural formula

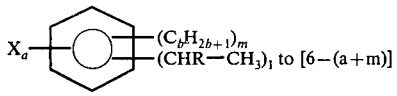

wherein X represents halogen; R represents hydrogen, methyl, or ethyl; $b$ represents 1 or 2; and $a$ and $m$ each represents 0, 1, or 2. When the aromatic hydrocarbon in the liquid sorbent is benzene, the alkylated aromatic compounds have the structural formula

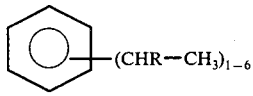

When the aromatic hydrocarbon is benzene and the olefin is ethylene, the alkylated aromatic compounds have the structural formula

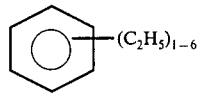

Polyalkylated benzenes that have more than three alkyl substituents on the aromatic ring have only slight solubility in the liquid sorbent, and they tend to form deposits in the cooler parts of the apparatus. Unlike the mono-, di-, and trialkylated compounds, the polyalkylated benzenes are too high boiling to be useful as the stripping gas that separates the olefins from the liquid sorbent.

The olefins also undergo polymerization in the liquid sorbent to form small amounts of olefin oligomers that have molecular weights in the range of about 100 to 1000 and that have only limited solubility in the liquid sorbent. In most cases, the liquid sorbent contains at least 10 parts by weight of alkylated aromatic compounds per part by weight of olefin oligomers formed as a reaction by-product.

The alkylation and polymerization reactions that yield the reaction by-products are catalyzed by the small amounts of aluminum chloride and other acidic compounds that are present in the liquid sorbent. They are also promoted by the elevated temperatures that are often used to decomplex the relatively-stable complexes formed by the olefins and the bimetallic salt complex.

In the practice of this invention, a portion of the stripped liquid sorbent, which contains the aforementioned bimetallic complex, aromatic hydrocarbon or halogenated aromatic hydrocarbon, and impurities that comprise alkylated aromatic compounds, is removed from the system, purified by removing alkylated aromatic compounds from it, reconstituted, and returned to the system where it is used to remove additional amounts of olefins and other complexible ligands from the gas feedstream. The portion of the liquid sorbent that is treated in this way may constitute from about 5% to 50% of the volume of liquid sorbent in the system. It is generally preferred that 10% to 20% by volume of the liquid sorbent be removed from the system and purified.

The impurity-containing stripped sorbent that has been removed from the system is purified by subjecting it first to flash distillation at atmospheric pressure to a temperature in the range of 80° C.-135° C. to remove from it a fraction that is rich in aromatic hydrocarbon or halogenated aromatic hydrocarbon and then to a flash distillation at a pressure in the range of 10 torr to 100 torr to a temperature in the range of 100° C. to 160° C. to remove from it a fraction that is rich in mono- and/or dialkylated aromatic compounds.

Following the flash distillation steps, sufficient aromatic hydrocarbon or halogenated aromatic hydrocarbon is added to the distillation residue to replace the materials that have been removed from it by distillation. The reconstituted purified liquid sorbent is then returned to the system where it is combined with the unpurified portion of the liquid sorbent. Sorbent that has been purified in this way can be used for long periods of time without build-up of those amounts of polyalkylated aromatic compounds that interfere with the efficient operation of the process and necessitate the replacement of the liquid sorbent.

The purification of the liquid sorbent may be carried out as a continuous or batch process.

In a preferred embodiment of this invention, a liquid sorbent that is a solution of cuprous aluminum tetrachloride·benzene in benzene and that has been used in a process for the removal of ethylene from a gas feedstream until it contains more than 15% by weight, and in many cases more than 25% by weight, of ethylbenzenes is purified by removing from it a portion that constitutes about 10% to 20% of the volume of the liquid sorbent; subjecting the separated portion of the liquid sorbent to flash distillation under atmospheric pressure to a temperature in the range of 80°-135° C., preferably 120°-135° C., to distill off a fraction that is rich in benzene and other volatile compounds; flash distilling the residue of the first flash distillation at a pressure of 10 torr to 100 torr, preferably 40 torr to 75 torr, to a temperature in the range of 100°-160° C., preferably in the range of 130°-150° C., to distill off a fraction that is rich in ethylbenzene; and adding to the residue of the second flash distillation a volume of benzene that is sufficient to replace the volumes of benzene, ethylbenzene, and other organic compounds removed in the two flash distillations. The reconstituted purified liquid sorbent is returned to the system where it is combined with the unpurified portion of the liquid sorbent to form a sorbent that contains about 2.4 moles of benzene, 0.6 mole of ethylbenzene, and less than 0.3 mole of other organic compounds per mole of cuprous aluminum tetrachloride.

The gases that distill from the liquid sorbent during the flash distillation at atmospheric pressure are passed through a cold water condenser to yield a first distillate that generally contains 90% to 95% by weight of benzene, 4% to 6% by weight of ethylbenzene, and small amounts of diethylbenzenes, triethylbenzenes, and toluene. This fraction may be used in combination with fresh benzene to bring the volume of the residue of the second flash distillation to the volume of the portion of impurity-containing liquid sorbent that was removed from the system and purified.

The gases that distill from the liquid sorbent during the flash distillation under subatmospheric pressure are passed through a cold water condenser to yield a second distillate that generally contains 25% to 40% by weight of benzene, 50% to 65% by weight of ethylbenzene, 5% to 10% by weight of diethylbenzenes, and small amounts of polyethylbenzenes, toluene, and ethyltoluenes. This distillate may be redistilled to separate ethylbenzene from its other components, or it may be used without further treatment as a reactant or solvent in various chemical processes.

During the flash distillation under subatmospheric pressure, the di-, tri-, tetra-, penta-, and hexaethylbenzenes that are in the liquid sorbent undergo transalkylation and/or dealkylation reactions that reduce the total amount of these compounds in the liquid sorbent from about 8%-15% to less than 5%.

The invention is further illustrated by the following examples.

EXAMPLE 1

A series of runs was carried out using the following procedure:

A. A liquid sorbent that contained 28.6 mole percent of cuprous aluminum tetrachloride and 71.4 mole percent of benzene was prepared by adding 1.1 moles of cuprous chloride to 1 mole of anhydrous aluminum chloride in benzene. The resulting solution was filtered to remove unreacted cuprous chloride and insoluble impurities from it. It then had a specific gravity of 1.30.

B. A gas feedstream that had the following composition:

| Ethylene | 19.6 mole percent |
|---|---|
| Carbon monoxide | 2.3 |
| Nitrogen | 70.7 |
| Benzene | 7.4 | was fed at ambient temperature and 19 psia into a column in which it was contacted with 73 gallons of the liquid sorbent whose preparation is described above. The ethylene and carbon monoxide in the feedstream reacted with the liquid sorbent as it traveled through the column to form a reaction mixture that was a solution of the ethylene-cuprous aluminum tetrachloride complex and the carbon monoxide-cuprous aluminum tetrachloride complex in the liquid sorbent. This solution was fed to a stripping column where it was brought into contact with benzene vapor at 95° C. The mixture of gases leaving the stripping column, which contained 90.4 mole percent of ethylene and 9.6 mole percent of benzene, was cooled to separate the benzene from the ethylene. More than 97% of the ethylene in the gas feedstream was recovered in this way. The stripped liquid sorbent was returned to the column where it reacted with additional amounts of ethylene and carbon monoxide in the gas feedstream.

A stream that consisted of 10% of the stripped liquid sorbent was passed continuously at the rate of 3.0 gallons per hour into a flash distillation vessel where it was heated by means of a steam coil to 135° C. at atmospheric pressure. The gases leaving the vessel were taken through a cooling water condenser and a fraction rich in benzene was collected. The hot flashed sorbent was fed at the rate of 1.86 gallons per hour to a vacuum flash vessel evacuated to 50 torr by means of a vacuum pump where it was heated to 145° C. Gases leaving the vacuum vessel were passed over chilled water coils to condense all of the ethylbenzene and benzene in them. The hot vacuum flashed sorbent was mixed with distillate collected during the atmospheric distillation and fresh benzene to dilute it and to replace the benzene, ethylbenzene, and other volatile compounds that had distilled off. The reconstituted purified sorbent was returned to the system where it was combined with the 90% of the stripped liquid sorbent that had not been purified. The resulting liquid sorbent contained 2.4 moles of benzene, 0.6 mole of ethylbenzene, and less than 0.3 mole of other organic compounds per mole of cuprous aluminum tetrachloride.

This purified liquid sorbent was found to be as effective as freshly-prepared liquid sorbent in removing ethylene and other complexible ligands from gas feedstreams.

EXAMPLE 2

The procedure described in Example 1C was used to purify a stripped liquid sorbent that was a solution of cuprous aluminum tetrachloride in benzene that contained as impurities alkylated benzenes. The liquid sorbent had a specific gravity of 1.31. Its organic phase had the following composition:

| | % by Weight |
|---|---|
| Benzene | 71.2 |
| Ethylbenzene | 16.9 |
| Diethylbenzene | 3.6 |
| Triethylbenzene | 0.8 |
| Tetraethylbenzene | 0.2 |
| Pentaethylbenzene | 0.5 |
| Hexaethylbenzene | 3.4 |
| Toluene | 2.2 |
| Ethyltoluene | 0.9 |
| Diethyltoluene | 0.2 |
| Triethyltoluene | 0.1 |

A 20% portion (154 pounds) of the liquid sorbent was heated under atmospheric pressure to 135° C. in 2 hours to distill off a benzene-rich fraction which weighed 41 pounds and then under the pressure of 20 torr to 132° C. in 2 hours to distill off an ethylbenzene-rich fraction which weighed 24 pounds. These distillates had the following composition:

| | % by Weight | |
|---|---|---|
| | 1st (atmospheric) Distillate | 2nd (vacuum) Distillate |
| Benzene | 93.6 | 33.8 |
| Ethylbenzene | 5.2 | 51.9 |
| Diethylbenzene | 0.2 | 8.2 |
| Triethylbenzene | <0.1 | 0.3 |
| Tetraethylbenzene | <0.1 | <0.1 |
| Pentaethylbenzene | <0.1 | <0.1 |
| Hexaethylbenzene | <0.1 | <0.1 |
| Toluene | 1.0 | 3.8 |
| Ethyltoluene | <0.1 | 2.0 |
| Diethyltoluene | <0.1 | <0.1 |
| Triethyltoluene | <0.1 | <0.1 |

Sixty-five pounds of benzene was added to the residue of the vacuum flash distillation to restore the liquid sorbent to its original volume. The reconstituted purified sorbent weighed 158 pounds and had a specific gravity of 1.24. Its organic phase had the following composition:

| | % by Weight |
|---|---|
| Benzene | 91.3 |
| Ethylbenzene | 3.2 |

-continued

|  | % by Weight |
|---|---|
| Diethylbenzene | 4.0 |
| Triethylbenzene | 1.1 |
| Tetraethylbenzene | <0.1 |
| Pentaethylbenzene | <0.1 |
| Hexaethylbenzene | <0.1 |
| Toluene | 0.1 |
| Ethyltoluene | 0.3 |
| Diethyltoluene | <0.1 |

The reconstituted purified liquid sorbent was returned to the system where it was combined with the 80% of the stripped sorbent that had not been purified. The resulting purified liquid sorbent was used to remove additional amounts of ethylene and other complexible ligands from the gas feedstream.

What is claimed is:

1. In the process for the separation of olefins having 2 to 4 carbon atoms from a gas feedstream wherein (a) the feedstream is contacted with a liquid sorbent that is a solution in an aromatic hydrocarbon or halogenated aromatic hydrocarbon of a bimetallic salt complex having the formula $$M_I M_{II} X_n \cdot \text{Aromatic}$$

wherein $M_I$ is a Group I-B metal, $M_{II}$ is a Group III-A metal, X is halogen, $n$ is the sum of the valances of $M_I$ and $M_{II}$, and Aromatic is a monocyclic aromatic hydrocarbon or halogenated aromatic hydrocarbon having 6 to 12 carbon atoms, thereby forming a reaction mixture that comprises a solution of a complex of the olefin and the bimetallic salt complex in the liquid sorbent, (b) the reaction mixture is separated from the feedstream, (c) the olefin is separated from the liquid sorbent in the reaction mixture, and (d) the liquid sorbent is recycled to Step (a), the improvement that comprises removing from the liquid sorbent impurities that are alkylated aromatic compounds by means of a purification process that comprises the following steps:

(i) dividing the liquid sorbent from which the olefin has been separated in Step (c) into a first portion that comprises 50% to 95% by volume of the liquid sorbent and a second portion that comprises 5% to 50% by volume of the liquid sorbent;

(ii) recycling the first portion of the liquid sorbent to Step (a);

(iii) heating the second portion of the liquid sorbent under atmospheric pressure to a temperature in the range of 80° C. to 135° C., thereby separating a fraction that is rich in aromatic hydrocarbon or halogenated aromatic hydrocarbon from the first residue;

(iv) heating the first residue under a pressure of 10 torr to 100 torr to a temperature in the range of 100° C. to 160° C., thereby separating a fraction that is rich in alkylated aromatic hydrocarbon or alkylated halogenated aromatic hydrocarbon from the second residue;

(v) adding to the second residue an amount of aromatic hydrocarbon or halogenated aromatic hydrocarbon that is substantially equal in volume to the sum of the volume of the fraction rich in aromatic hydrocarbon or halogenated aromatic hydrocarbon that was separated in Step (iii) and the volume of the fraction rich in alkylated aromatic hydrocarbon or alkylated halogenated aromatic hydrocarbon that was separated in Step (iv), thereby forming a reconstituted purified liquid sorbent; and (vi) recycling the reconstituted purified liquid sorbent to Step (a).

2. The process of claim 1 wherein the liquid sorbent is a solution of cuprous aluminum tetrachloride in an aromatic hydrocarbon or halogenated aromatic hydrocarbon.

3. The process of claim 1 wherein the liquid sorbent is a solution of cuprous aluminum tetrachloride·benzene in benzene.

4. The process of claim 1 wherein the olefin that is separated from the gas stream is ethylene.

5. The process of claim 1 wherein the Step (i) the liquid sorbent is divided into a first portion that comprises 80% to 90% by volume of the liquid sorbent and a second portion that comprises 10% to 20% by volume of the liquid sorbent.

6. The process of claim 3 wherein in Step (iii) the liquid sorbent is heated under atmospheric pressure to a temperature in the range of 120° C. to 135° C.

7. The process of claim 3 wherein in Step (iv) the first residue is heated under a pressure of 40 torr to 75 torr to a temperature in the range of 130° C. to 150° C.

8. The process of claim 3 wherein the aromatic hydrocarbon or halogenated aromatic hydrocarbon that is added to the second residue in Step (v) comprises the fraction rich in aromatic hydrocarbon or halogenated aromatic hydrocarbon that was separated in Step (iii).

9. The process of claim 3 wherein the reconstituted purified liquid sorbent formed in Step (v) is combined with the first portion into which the liquid sorbent is divided in Step (i) to form a purified liquid sorbent that contains about 2.4 moles of benzene, 0.6 mole of ethylbenzene, and less than 0.3 mole of other organic compounds per mole of cuprous aluminum tetrachloride and said purified liquid sorbent is recycled to Step (a).

10. The process of claim 1 wherein the purification process of Steps (i)-(vi) is carried out as a continuous process.

* * * * *